United States Patent [19]

Kuhn et al.

[11] Patent Number: 4,522,190

[45] Date of Patent: Jun. 11, 1985

[54] FLEXIBLE ELECTROCHEMICAL HEATER

[75] Inventors: William E. Kuhn, Lexington, Ky.; Kwoh H. Hu, Weston, Mass.; Stanley A. Black, Ventura, Calif.

[73] Assignee: University of Cincinnati, Cincinnati, Ohio

[21] Appl. No.: 548,541

[22] Filed: Nov. 3, 1983

[51] Int. Cl.$^3$ ................................................ F24J 1/00
[52] U.S. Cl. .................................. 126/263; 126/204; 44/3 R; 204/248
[58] Field of Search ................. 126/263, 204; 128/254, 128/399, 403; 252/74, 188.1; 44/3 R, 3 A, 3 B, 3 C; 204/248; 423/658

[56] References Cited

U.S. PATENT DOCUMENTS

| 1,899,286 | 2/1933 | Meagher | 126/263 |
| 3,512,516 | 5/1970 | Glass et al. | 126/263 |
| 3,683,889 | 8/1972 | Hoffman | 126/263 |
| 3,774,589 | 11/1973 | Kober | 126/263 |
| 3,874,504 | 4/1975 | Verakis | 206/219 |
| 3,942,511 | 3/1976 | Black et al. | 126/248 |
| 3,980,070 | 9/1976 | Krupa | 126/263 |
| 3,993,577 | 11/1976 | Black et al. | 252/188 |
| 4,017,414 | 4/1977 | Black et al. | 252/188 |
| 4,067,313 | 1/1978 | Donnelly | 126/263 |
| 4,080,953 | 3/1978 | Mitchell et al. | 126/263 |
| 4,106,477 | 8/1978 | Feld | 126/204 |
| 4,106,478 | 8/1978 | Higashijima | 126/263 |
| 4,205,957 | 6/1980 | Fujiwara | 44/3 R |
| 4,264,362 | 4/1981 | Sergev et al. | 75/243 |
| 4,404,820 | 9/1983 | Romaine | 128/399 |

Primary Examiner—Samuel Scott
Assistant Examiner—Helen A. Odar

[57] ABSTRACT

This invention is for an inexpensive flexible heater material (heat pad) for food heating, medical compresses and the like. The heat pad is a composite material consisting of a supercorroding metallic alloy powder dispersed throughout a porous polyethylene matrix. The supercorroding alloy material consists of a powdered alloy of magnesium and iron which is produced by high energy powder metallurgical milling techniques. Pressureless sintering of a mixture of the supercorroding alloy powders with UHMW polyethylene powder results in the formation of a flexible porous matrix material with active ingredients therein that are readily activated with a suitable electrolyte fluid.

25 Claims, 11 Drawing Figures

INNER FOIL PAPER SUPERIMPOSED OVER AND SEALED TO A

HEATER PADS ATTACHED TO POLY FOIL PAPER

HEATER PADS ENCLOSED IN TEA BAG PAPER

FLEXIBLE ELECTROCHEMICAL HEATER

This invention was made with Government support and the Government has certain rights in the invention.

BACKGROUND OF THE INVENTION

This invention relates to electrochemical heating devices and more particularly to a strong, compact, conformable, self-contained, non-toxic and flameless heating source for use in heating military field rations, as heating pads, as medical hot compresses and body warmers.

Several prior art heating sources having somewhat flexible construction have been proposed. The U.S. Pat. Nos. 3,774,589 to Kober, and 3,942,511 to Black, et al, show heat cell structures which are fabricated from separate components and then assembled. However, the integrity of these structures is destroyed if the constructions are damaged by improper handling or if cut, and their manufacture is expensive. Also, U.S. Pat. Nos. 4,080,953 to Mitchell, 3,980,070 to Krupa, and 3,874,504 to Veraks, provide limited flexibility from loose powdered material which requires a pouch or other container to hold the reactants and concentrate the heat. The sandwich structure in Black, et al, U.S. Pat. No. 3,942,511, while providing flexibility is complicated, less efficient and difficult to manufacture. These and other prior art devices lack ease in manufacture, material strength or flexibility to conform to any surface.

SUMMARY OF THE INVENTION

A heating device of the present invention involves the unique construction of a flexible heating pad material which utilizes a totally integrated structure consisting of polymeric materials (such as polyethylene) and supercorroding alloys. The heating pad material is formed in a manner which provides: porosity to allow controlled wetting of the supercorroding alloys; formability to allow ease of manufacture to any shape; unity of manufacture which allows a simple process to be used to blend and form the mixture of particles into a desired shape while sintering the formed pad into a strong flexible material without the need for other components such as pouches to hold active constituents; flexibility to permit conforming to any surface to be heated; and, compactness to provide light-weight high-density heating.

It is, therefore, an object of the present invention to provide a simple, low cost fabrication and self-contained heat source which is easily activated, non-complex, light-weight, compact, strong, and stands alone without the need for containment packaging of active materials.

Another object of this invention is to provide a simple effective technique for heating military field rations and the like which is not toxic, is self-contained, is compact, and does not produce a flame.

A further object is to provide a heat source using micro electrochemical cells for warming various parts of the human body.

Other objects, advantages and novel features of the invention will become apparent from the following detailed description of the invention when considered in conjunction with the accompanying drawings.

DESCRIPTION OF THE PREFERRED EMBODIMENTS

Figure 1:
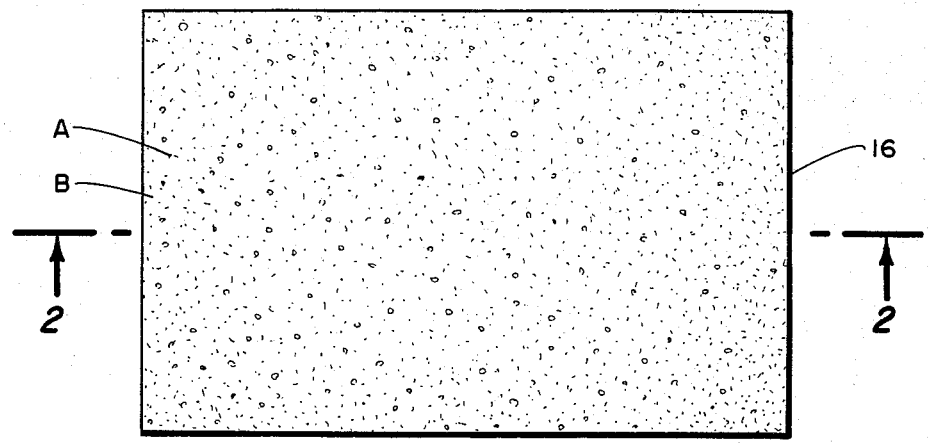
FIG. 1 illustrates a sintered porous matrix of polymeric material with supercorroding metallic alloy powders dispersed throughout.
Figure 2:
FIG. 2 is a sectional view taken along line 2—2 of FIG. 1.

The flexible heat pad of this invention is a composite material consisting of a supercorroding metallic alloy powder A dispersed throughout a porous matrix of polymeric material B, such as polyethylene, as shown in FIGS. 1 and 2. The supercorroding alloy material (active ingredients) preferably consist of a powdered alloy of magnesium and iron which is produced by high energy powder metallurgical milling techniques, similar to those used in the teachings of Sergev, et al, U.S. Pat. No. 4,264,362. The present invention, however, uses a combination of polyethylene powders and powdered supercorroding alloys blended together. Pressureless sintering of the mixture results in the formation of a porous flexible material which assumes the shape of the mould. Thin porous heating pads of any desired shape are readily made in this manner. When wetted with a suitable electrolyte, such as sodium chloride solution, heat is rapidly and efficiently produced.

Typical heater pads, FIGS. 1 and 2, can be constructed from magnesium with 5 atomic percent iron supercorroding alloy powders blended with ultra-high-molecular-weight (UHMW) polyethylene powder (e.g., 4 grams Mg-5at.%Fe supercorroding alloy powders blended with 10 grams UHMW polyethylene powder). Other proportions of supercorroding alloy to polyethylene can be used, as well as other compositions and additional elements. The mixture is placed into a metal mould of desired shape and packed to form a uniform pad. The mould is then heated in an oven for approximately 20 minutes at 168° C. Heating causes the UHMW polyethylene powder to sinter and adhere to the MgFe alloy, which after cooling forms a strong and flexible pad with sufficient porosity to allow water or electrolyte to penetrate and wet the alloy. The composite blend of powders can be sintered with or without pressure to provide a material of variable density depending on the conditions of sintering.

The heat pad technology can be used to produce heaters having a variety of useful shapes and sizes. Heaters can be inexpensively fabricated in a variety of useful shapes including blocks, plates, rods and more complex forms. The quantity and rate of heat produced can be adjusted by varying the quantity and content of the active supercorroding alloy contained within the polyethylene matrix and the composition of the composite.

Figure 3:
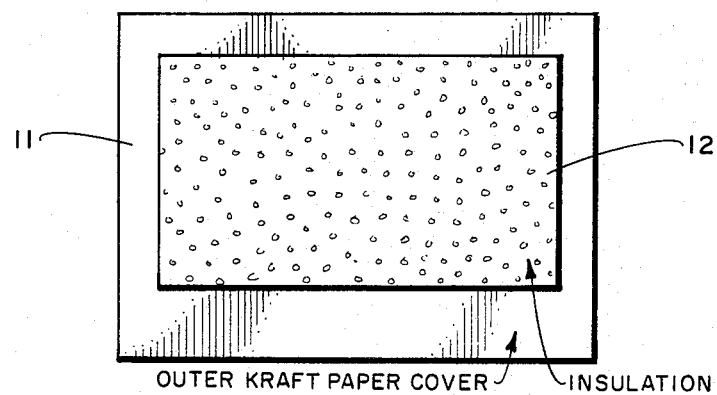
FIG. 3 shows the outer cover and insulation in the assembly sequence for a heater pouch.
Figure 4:
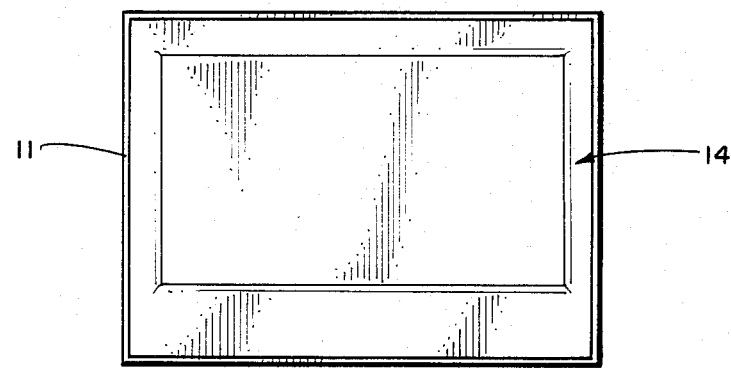
FIG. 4 shows an inner barrier with a plastic covering superimposed over the assembly of FIG. 3.
Figure 5:
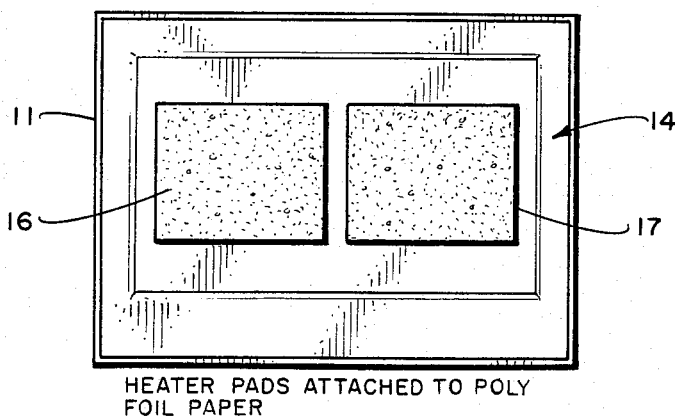
FIG. 5 shows heater pads attached to the plastic covering surface of the assembly in FIG. 4.
Figure 6:
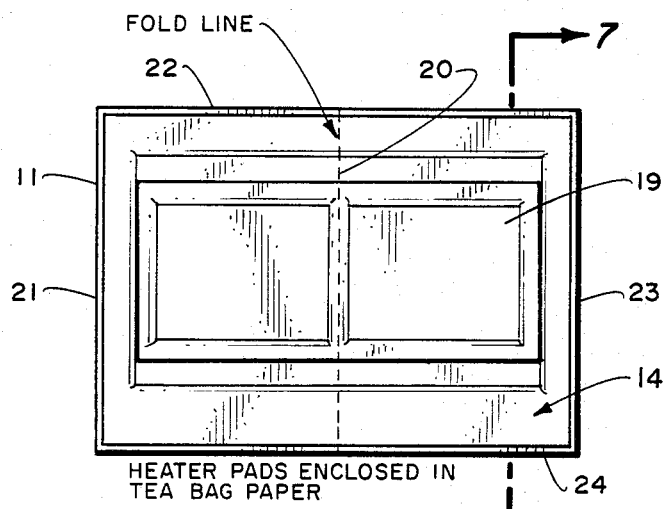
FIG. 6 shows the heater pads enclosed with a porous paper layer sealed to the plastic covering of the inner barrier.
Figure 7:
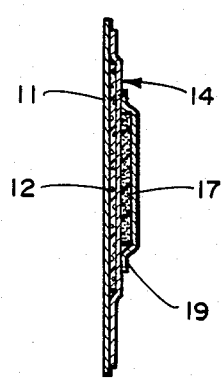
FIG. 7 is a cross-sectional view along line 7—7 of FIG. 6.

The heat pads are particularly applicable to use in field ration heaters, for food warming and the like and for example, a preferred construction and assembly for a field ration heater pouch 10 is illustrated in FIGS. 3 through 8. As shown in FIG. 3, an outer cover of kraft-/polythylene laminate paper 11, for example, has a layer of plastic foam insulation 12 (e.g. 1/16 inch thick Dupont microfoam) secured thereto to minimize heat transfer. A barrier 14 is superimposed over the insulation layer 12 and sealed to the edges of outer cover 11, as shown in FIG. 4. Barrier 14 (e.g. kraft foil paper) comprises a paper layer 14a, an aluminum foil layer 14b and an inner plastic covering 14c (see FIG. 8) to prevent moisture from entering pouch 10 during storage, and to keep the electrolyte in the pouch during activation. The inner plastic covering 14c (e.g., polyethylene) of barrier 14 permits heat sealing together of the pouch edges when folded face to face, as discussed below. Heater pads 16 and 17, formed from supercorroding alloys and UHMW polyethylene powders as described above, are attached to the barrier 14 layer as shown in FIG. 5. Tea bag type paper 19 is then placed over heat pads 16 and 17 and heat sealed along its edges to barrier 14 (see FIG. 6). Tea bag paper 19 improves the performance of the heat pouches by: serving as a wick to transport the salt solution to the active heater element; operating to slow the reaction between the salt solution and the heater pads by preventing excessive wetting of the heater pads; containing loose particles and debris originating from the heater pad due to rough handling and/or from the pad while activated; and facilitates entry of a food packet into the heater pouch by preventing snagging on the edge of a heating pad. FIG. 7 shows, in cross-section, the layers of the completed assembly with all the components of the assembly sequence of FIGS. 3-6.

Figure 8:
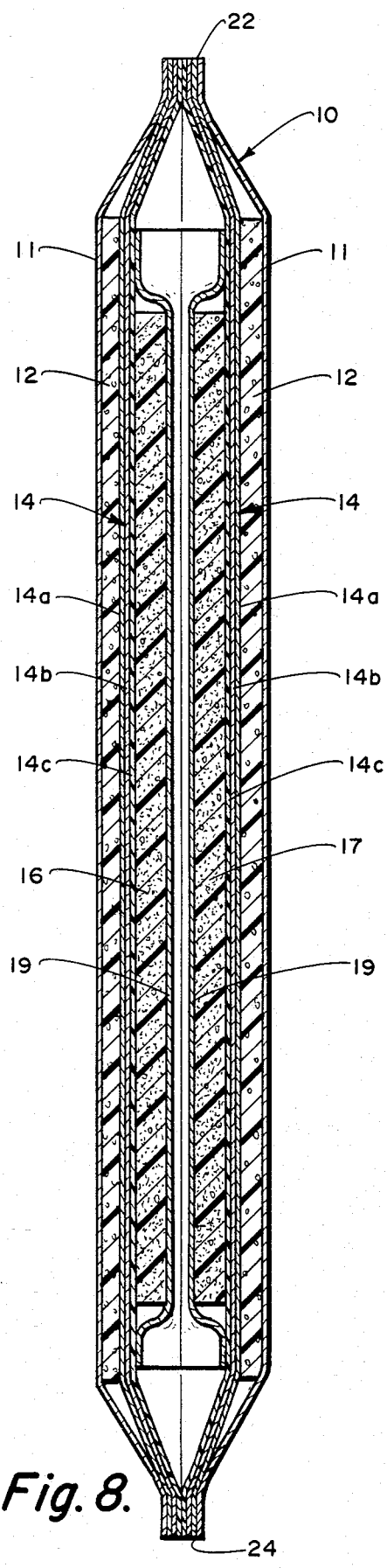
FIG. 8 is a cross-sectional view of a heater pouch formed after folding and sealing the assembly of FIG. 6.

The assembly shown in FIG. 6 is then folded along line 20 and sealed along edges 21, 22, 23, and 24 by heat sealing or with a suitable cement to form a heater pouch as shown in FIG. 8. Edges 21 and 23 are sealed together; the two halves of edge 22 are sealed together and the two halves of edge 24 are sealed together. Sealed edge 22 can be notched to assist in tearing off at time of use. If desired, a heater pouch can be constructed using a heat pad 16 on one side only.

Figure 9:
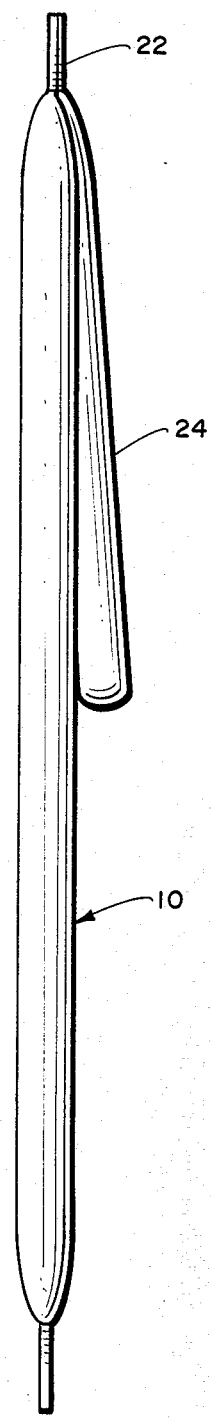
FIG. 9 is a side view of a heater pouch assembly with an electrolyte pouch attached.

An electrolyte pouch 24, fabricated of waterproof material, containing 30 ml of 23.3% NaCl and $H_2O$, for example, can be attached to the heater pouch 10 at the top edge 22, as shown in FIG. 9.

Operation of the electrochemical food ration heater is as follows: First, the electrolyte pouch 24 is removed from the heater pouch 10 by pulling it apart from edge 22. Second, the top of the heater pouch is torn off along the notched end 22. Heater pouch 10 can then be opened and a field ration (e.g. food in a flexible foil packet) inserted into the heater envelope. The food packet is pushed all the way to the bottom of the heater pouch, with the field ration food packet unopened. A corner then can be torn off the electrolyte pouch 24 and the contents poured into the heater pouch. After the electrolyte is poured into the heater pouch, the open end of the heater pouch is folded over to retain as much heat as possible. Activation of the heating process is almost immediate following addition of the electrolyte. The heating reaction involves the corrosion of Magnesium in general accordance with the reaction. $Mg + H_2O$ $Mg(OH)_2$ + Heat. Approximately 1600 w-hr/lb of supercorroding alloy of heat is available.

Figure 10:
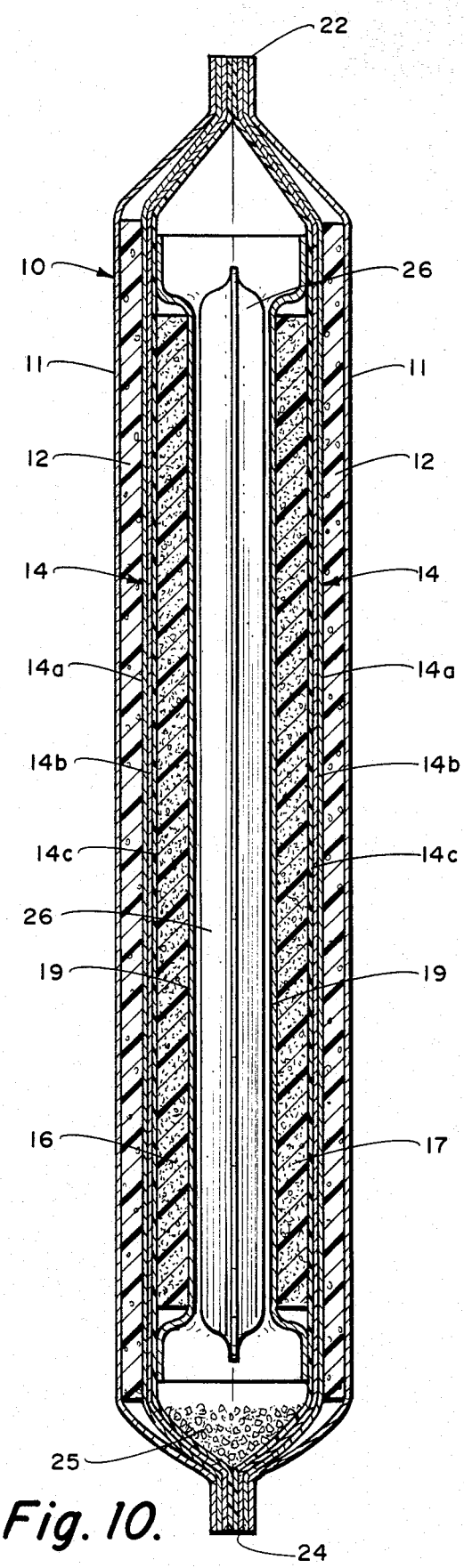
FIG. 10, illustrates in cross-section, a heater pouch incorporating a flexible food packet to be heated.

Alternately, dry salt (NaCl) 25 can be placed inside the heater pouch 10 and water added to activate the supercorroding alloy materials. This method eliminates the need for an electrolyte pouch 24 and reduces the total heater package weight. Also, a flexible foil food packet 26 can be incorporated into the heater pouch construction in addition to dry NaCl. In this alternate configuration, shown in FIG. 10, it is only necessary to add water to create an electrolyte solution for activating the heater and heat the food packet. The food ration heater described above, using 4 grams Mg-5at%Fe, is capable of raising 151 grams of food approximately 55° C.; with an initial temperature of 21° C., and final temperature after 10 minutes of 76° C. Higher temperatures can be achieved by using heater pads with more supercorroding alloy. Some heat escapes the package in the form of steam and Hydrogen gas. The Hydrogen gas dissipates rapidly and does not present a hazard for individual package use. Attempts to ignite the Hydrogen using an open flame and spark have failed to produce ignition. Heat from the heater pads is transferred to the food by conduction. Squeezing the food packet during heating helps speed the warming action. Left in the heater pouch, the food stays warm for extended periods of time. Once warm the top can be torn off the food packet while still in the heater pouch and the food consumed.

The heat pads can be constructed in many different shapes, physical dimensions, and of different supercorroding alloy constituents, such as Ni Cathode, $MnO_2$ Cathode, and other Anodic Materials such as Al. Also, heating pads can be constructed on which only one side is insulated (a cross-section of which is similar to FIG. 7) and the uninsulated side is placed against the item to be heated, such as a pot or coffee cup, etc.

Where the generation of hydrogen may be considered a problem, hydrogen can be eliminated or drastically reduced by catalytic recombination with the oxygen in air.

Hydrogen can be removed catalytically by the reaction

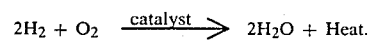

$$2H_2 + O_2 \xrightarrow{catalyst} 2H_2O + \text{Heat.}$$

Figure 11:
FIG. 11 is a cross-sectional view of a flexible catalytic pad for eliminating/reducing hydrogen and generating heat.

This both removes hydrogen and provides additional heat, thereby reducing the amount of supercorroding alloy needed to raise the temperature of the food heating pouch to the desired temperature. A standard catalytic material consisting of one part $MnO_2$ to 0.06 part Pd catalyzed carbon blended with UHMW polyethylene in the ratio of approximately 2 parts catalyst material to 10 parts polyethylene can be used to make a flexible catalytic oxidizer material. Flexible catalytic pads, such as shown in FIG. 11, can be made from mixtures of catalytic material and UHMW polyethylene, and, like heat pads 16 and 17, formed and the food temperature or ΔT of a food pouch warmed in a heater pouch. Iron contents less than 1 atomic percent result in a sharp drop in food pouch temperatures. The volume of salt solution added to the heater pouch affects the temperature of the food pouch and $\Delta T$.

Potential applications for the flexible heater material are listed for four classes of applications:

a. Marine Release Devices: Sampling sea water, timing devices, scuttling plugs, recording temperature, salinity, oxygen, depth, cable releases, etc.

b. Thermal Devices: Portable source of heat for divers, emergency heating (e.g. hypothermia), melting holes in artic ice fields, hand and boot warmers, instrument heating, survival and first aid kits (ocean, aircraft, troops, expeditions, hunters, back-packers, space vehicles, etc.), medical applications such as heating pads and wraps.

c. Energy Source: Fuel cells ($H_2$), space vehicles, remote instrumentation, hydrogen fueled vehicles, gas driven motors, heating pouched food and food trays for field kitchens, etc.

d. Buoyancy Devices: Salvage operations ($H_2$), weather balloons.

The sintered mixture of ultra high molecular weight polyethylene and supercorroding alloy powders forms a strong, sintered. $MnO_2$-Pd-C catalyst powder mixtures milled for 15 minutes produced the highests temperature change, $\Delta T$, and additional food packet temperature.

Both the flexible composite heater material incorporating supercorroding alloy powders and the flexible composite catalyst material can be formed into different shapes such as sheets, blocks, plates, and more complicated shapes by methods that have been used in powder metallurgy.

Both $AgO_2$-$MnO_2$ and Pd-C-$MnO_2$ mixtures can be useful as low cost catalytic materials for the elimination of evolved hydrogen and heating the food pouches. The capacity to absorb and the rate of absorption is substantially enhanced by high energy ball milling Pd-C-$MnO_2$ powder mixtures.

Relatively small amounts of sodium chloride in solution are required to activate the heat pads and sustain the reaction which the Mg-Fe alloy in the flexible pads. The minimum concentration of NaCl required to produce a $\Delta T$ of $\pm 57° \pm 3°$ C. is about 2 percent while as little as 0.5 wt. percent produces a $\Delta T$ of 54° C. Concentrations less than the latter produce a sharp decline in $\Delta T$. The food pouch temperature and $\Delta T$ increases at a decreasing rate with increasing Mg-5at/°Fe alloy powder content of the heater pads from approximately 75° and 50° respectively at 6 grams to 90° and 64° C. respectively at 14 grams of alloy powder per heater pad. Iron contents of the Mg-Fe alloy between 1 and 5 atomic percent have no significant effect on increasing or decreasing flexible, porous, unitary matrix structure which provides a self-contained heat source when wetted with a suitable electrolyte. This flexible heater material can readily be stored in sealed containers until needed for use in any of a variety of applications, such as discussed above.

Obviously many modifications and variation of the present invention are possible in light of the above teachings. It is therefore to be understood that within the scope of the appended claims the invention may be practiced otherwise than as specifically described.

What is claimed is:

1. An electrochemical heating device capable of generating heat at a controlled rate, comprising:

a. a container adapted to be placed against an article so as to transfer heat developed within the container to the article;
b. at least one stand-alone flexible heating element disposed within said container;
c. said flexible heating element comprising a totally integrated sintered composite structure of blended powdered polymeric material and supercorroding metallic alloy powders dispersed throughout in the form of a porous matrix;
d. means for sealing said container, making the container air-impermeable;
e. said flexible heating element being operable to be wetted and activated with an electrolyte to generate heat through electrochemical reactions.

2. An electrochemical heating device as in claim 1 wherein said container is an insulated, flexible, air-impermeable envelope.

3. An electrochemical heating device as in claim 1 wherein a dry electrolyte means is included within said container; said dry electrolyte means being adapted to create an electrolyte solution upon adding water thereto for activating the flexible heating element to generate heat.

4. An electrochemical heating device as in claim 1 wherein sodium chloride solution is added as an electrolyte to activate the heating element for generating heat.

5. An electrochemical heating device as in claim 1 wherein said supercorroding alloy powders are constructed from magnesium with 1 to 5 atomic percent iron and produced by high energy metallurgical milling.

6. An electrochemical heating device as in claim 1 wherein said powdered polymeric material is ultra high molecular weight polyethylene.

7. An electrochemical heating device as in claim 1 wherein said sintered porous matrix structure is constructed from 4 grams of supercorroding alloy powders per 10 grams powdered polymeric material.

8. An electrochemical heating device as in claim 1 wherein said heating element is covered within said container with a wick means for transporting electrolyte solution to the heating element and preventing excessive wetting of the heating element with electrolyte solution.

9. An electrochemical heating device as in claim 1 wherein said wick means is tea bag type paper.

10. An electrochemical heating device as in claim 1 wherein said container is in the form of a pouch into which an article to be heated is inserted.

11. An electrochemical heating device as in claim 2 wherein said container is in the form of a flexible pouch in which a sealed food packet is incorporated during construction.

12. An electrochemical heating device as in claim 11 wherein a dry electrolyte means is included within said container; said dry electrolyte means being adapted to create an electrolyte solution upon adding water thereto for activating the flexible heating element to generate heat for heating said food packet.

13. An electrochemical heating device as in claim 1 wherein a flexible catalytic means is provided within said container for both reducing hydrogen generated by said heating means following activation by an electrolyte and generating additional heat.

14. A flexible composite, stand-alone, electrochemical heating element for the generation of heat and hydrogen, adaptable for use both as a thermal device and energy source, comprising:

a. a blended mixture of powdered polymeric material and supercorroding metallic alloy powders dispersed throughout said material;
b. said mixture being sintered to form an integrated flexible porous matrix structure;
c. said flexible sintered porous matrix structure being operable to be wetted and activated with an electrolyte to generate heat and hydrogen through electrochemical reactions.

15. An electrochemical heating device as in claim 14 wherein said supercorroding alloy powders are constructed from magnesium with 1 to 5 atomic percent iron and produced by high energy metallurgical milling.

16. An electrochemical heating device as in claim 14 wherein said powdered polymeric material is ultra high molecular weight polyethylene.

17. An electrochemical heating device as in claim 14 wherein said sintered porous matrix structure is constructed from 4 grams of supercorroding alloy powders per 10 grams powdered polymeric material.

18. An electrochemical heating device as in claim 14 wherein said electrolyte is sodium chloride solution.

19. An electrochemical heating blanket capable of producing heat at a controlled rate, comprising:
a. a flexible envelope adapted to be wrapped around an article so as to transfer heat developed within the envelope to the article;
b. at least one stand-alone flexible heating element disposed within said envelope;
c. said flexible heating element comprising a totally integrated sintered composite structure of blended powdered polymeric material and supercorroding metallic alloy powders dispersed throughout in the form of a porous matrix;
d. said flexible heating element being operable to be wetted and activated with an electrolyte to generate heat through electrochemical reactions.

20. An electrochemical heating device as in claim 19 wherein said supercorroding alloy powders are constructed from magnesium with 1 to 5 atomic percent iron and produced by high energy metallurgical milling.

21. An electrochemical heating device as in claim 19 wherein said powdered polymeric material is ultra high molecular weight polyethylene.

22. An electrochemical heating device as in claim 19 wherein said sintered porous matrix structure is constructed from 4 grams of supercorroding alloy powders per 10 grams powdered polymeric material.

23. An electrochemical heating device as in claim 19 wherein said heating element is covered with a wick means for uniformly wetting said heating element with electrolyte solution.

24. An electrochemical heating device as in claim 23 wherein said wick means is tea-bag-type paper.

25. An electrochemical heating device as in claim 19 wherein one side of said heating blanket is insulated.

* * * * *